United States Patent
Doerr

(10) Patent No.: US 8,974,397 B2
(45) Date of Patent: Mar. 10, 2015

(54) DISLOCATION SENSOR

(71) Applicant: Biotronik SE & Co. KG, Berlin (DE)

(72) Inventor: Thomas Doerr, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 114 days.

(21) Appl. No.: 13/896,013

(22) Filed: May 16, 2013

(65) Prior Publication Data

US 2013/0345536 A1  Dec. 26, 2013

Related U.S. Application Data

(60) Provisional application No. 61/661,813, filed on Jun. 20, 2012.

(51) Int. Cl.
| | |
|---|---|
| *A61N 1/00* | (2006.01) |
| *A61N 1/37* | (2006.01) |
| *A61N 1/05* | (2006.01) |
| *A61N 1/08* | (2006.01) |
| *A61N 1/368* | (2006.01) |
| *A61B 5/042* | (2006.01) |
| *A61N 1/39* | (2006.01) |

(52) U.S. Cl.
CPC ................ *A61N 1/371* (2013.01); *A61N 1/056* (2013.01); *A61N 1/08* (2013.01); *A61N 1/3686* (2013.01); *A61N 1/3704* (2013.01); *A61N 2001/0585* (2013.01); *A61B 5/042* (2013.01); *A61N 1/3937* (2013.01)
USPC ........................................................ 600/527

(58) Field of Classification Search
USPC ......... 607/4, 17, 23, 24, 27, 28; 600/374, 513
See application file for complete search history.

(56) References Cited

U.S. PATENT DOCUMENTS

| | | | |
|---|---|---|---|
| 5,910,120 A | 6/1999 | Kim et al. | |
| 6,347,249 B1 * | 2/2002 | Kim et al. ........................ | 607/27 |
| 7,664,550 B2 | 2/2010 | Eick et al. | |
| 2007/0255327 A1 | 11/2007 | Cho et al. | |
| 2012/0143278 A1 * | 6/2012 | Ryu et al. ......................... | 607/28 |

FOREIGN PATENT DOCUMENTS

WO  2012/128836  9/2012

OTHER PUBLICATIONS

European Search Report, dated Oct. 22, 2013, 6 pages.

* cited by examiner

*Primary Examiner* — Catherine Voorhees
*Assistant Examiner* — Nadia A Mahmood
(74) *Attorney, Agent, or Firm* — ARC IP Law, PC; Joseph J. Mayo

(57) ABSTRACT

A cardiac therapy device and/or a cardiac monitoring device connected to at least one electrode lead that includes at least one first sensing electrode pole and at least one second sensing electrode pole. The at least one first and second sensing electrode poles move relative to one another during operation of the device. The device further includes a dislocation detection unit connected directly or indirectly to the at least one first and second sensing electrode poles. In order to detect dislocation, the dislocation detection unit evaluates detection times at the at least one first and second sensing electrode pole relative to one another. The detection times are ascribable to a cardiac event, such that the dislocation unit generates a dislocation signal if the relative time relationship of the detection times changes beyond a predetermined value, or a specifically determined value changes compared to a previously recorded reference value.

19 Claims, 7 Drawing Sheets

DISLOCATION SENSOR

This application claims the benefit of U.S. Provisional Patent Application 61/661,813, filed on 20 Jun. 2012, the specification of which is hereby incorporated herein by reference.

BACKGROUND OF THE INVENTION

1. Field of the Invention

At least one embodiment of the invention relates to an implantable cardiac therapy device and/or a cardiac monitoring device, such as a cardiac pacemaker or a cardioverter/defibrillator, which is capable of automatically detecting a dislocation of an electrode lead or an electrode pole.

2. Description of the Related Art

Implantable cardiac therapy devices and/or cardiac monitoring devices such as cardiac stimulators in the form of cardiac pacemakers or cardioverters/defibrillators are basically known. Such cardiac stimulators are typically connected to electrode leads that comprise stimulation electrodes and optionally defibrillation electrodes, placed in a ventricle or in the immediate vicinity thereof. Generally, using a stimulation electrode, and more specifically one or more stimulation electrode poles, a cardiac pacemaker may deliver an electrical stimulation pulse to the muscle tissue of a ventricle to thereby induce a stimulated contraction of the ventricle provided the stimulation pulse has sufficient intensity, and the cardiac muscle tissue, the myocardium, is not in a refractory phase during the delivery contraction of a ventricle that was stimulated in this manner is referred to within the scope of this description as a stimulated event. Also, a stimulation pulse that is sufficiently intense to induce a stimulation contraction of a ventricle is commonly referred to as an "above-threshold" stimulation pulse. If a natural contraction of the ventricle occurs, this is commonly referred to as a natural action or a natural or intrinsic event. A contraction of the right atrium of a heart, for instance, is commonly referred to as an atrial event that may be a natural atrial event, for example, or a stimulated atrial event when using an atrial cardiac pacemaker. Generally, a distinction may be made between natural and intrinsic events, and stimulated left ventricular events and stimulated right ventricular events.

Typically, local excitation of the myocardium propagates from the excitation site by conduction in the myocardium, resulting in depolarization of the muscle cells and thus contraction of the myocardium. After a brief period of time the muscle cells are typically repolarized and the myocardium therefore relaxes. During the phase of depolarization, the cardiac muscle cells are insensitive to stimulation, i.e. they are refractory. This period is commonly referred to as the refractory period. The electrical potentials associated with depolarization and repolarization may be sensed, and the variation thereof over time—referred to as an electrocardiogram, which can be evaluated.

Generally, in an electrocardiogram, action potentials that accompany a contraction of the ventricle and reflect depolarization of the cardiac muscle cells, are detected as a Q peak, while the repolarization of the cardiac muscle cells that accompanies the relaxation of the myocardium is reflected in a T wave.

The cardiac rhythm of a healthy individual is typically determined by the sinoatrial node that is controlled by the autonomic nervous system, and that stimulates the right atrium of a human heart and furthermore, via the AV node, the (right) ventricle of the heart. A natural cardiac rhythm originating in the sinoatrial node is commonly referred to as a sinus rhythm, and induces natural contractions of the particular ventricle, which may be detected as natural (intrinsic) events.

The natural (intrinsic) events are most commonly detected by determining the electrical potentials of the myocardium of the particular ventricle using sensing electrodes that are part of a corresponding electrode lead. The sensing electrode poles may also act as stimulation electrode poles, and may be used as a stimulation electrode pole and as a sensing electrode pole. Typically, two adjacent electrode poles may form a pair of sensing electrode poles. For example, a tip electrode and a ring electrode may be provided for sensing, such as sensing of intrinsic events, wherein the tip electrode is also used as the stimulation electrode pole. From the pair of sensing electrodes, a bipolar recording of an intracardial electrocardiogram (IEGM) may be obtained. In that case, sensing and stimulation take place in the ventricle using a ventricular electrode lead, and stimulation and sensing take place in the atrium, such as in the right atrium, using an atrial electrode lead that is separately connected to the cardiac stimulator. In addition, for example, a left ventricular electrode lead may be provided that typically extends via the coronary sinus and a lateral vein branching off of the coronary sinus and into the vicinity of the left ventricle. The left ventricular electrode lead may comprise a stimulation electrode and/or sensing electrode having a small surface area.

With respect to the terms used herein, it is noted that, within the scope of the invention, the terms stimulation electrode or sensing electrode may include a particular electrode pole at an electrode lead, wherein a part of an electrode delivers stimulation pulses and/or receives electrical potentials. It should also be pointed out that it is also common to refer to an electrode lead used for stimulation as a "stimulation electrode".

During operation of the cardiac stimulator, the sensing electrode poles may be connected to appropriate sensing units, that are designed to evaluate a particular electrocardiogram recorded using a sensing electrode pole, or using a pair of sensing electrode poles, and, in particular, to detect intrinsic atrial or ventricular events such as natural atrial or ventricular contractions. Typically, this takes place, for example, by comparison with a threshold value, wherein an intrinsic event is detected when a particular intracardial electrocardiogram exceeds a suitably specified threshold value.

If an electrode lead, including the sensing electrode poles thereof, should become dislocated, such as "slip" or "move", generally the amplitude and/or shape of signals obtained using the one or more sensing electrode poles may change, albeit not for physiological reasons. This poses a problem with respect to the reliable evaluation of signals that are recorded, and it is therefore desirable to detect a dislocation of an electrode lead and/or the electrode poles thereof, especially since a number of relevant therapy parameters may be derived from recorded signals.

On the basis of the frequency at which the atrial and ventricular events follow one another, the particular intrinsic atrial heart rate, such as an atrial frequency, or ventricular heart rate, such as a ventricular frequency, may be derived, thus enabling detection of tachycardias.

In the case of known demand pacemakers, the detection of natural events is also used to suppress, or inhibit, the delivery of stimulation pulses to a particular ventricle if the natural event is detected within a time window before the planned delivery of a stimulation pulse to the ventricle occurs. As common in the art, using rate-adaptive cardiac pacemakers, the point in time for delivery of a particular stimulation pulse is planned depending on a particular stimulation rate which should correspond to a patient's physiological demand, that is typically higher when exertion is greater, for instance. For this purpose, a cardiac stimulator may be equipped with one or more activity sensors, such as a Closed Loop Stimulation (CLS) sensor, which is described in greater detail below.

With respect to a dislocation of sensing electrode poles that may influence the sensing of events, approaches for detecting such a dislocation are known. Known approaches for detecting a dislocation of a stimulation electrode are based on the evaluation of the sensing amplitude, the electrode impedances and the pacing thresholds.

For example, U.S. Pat. No. 7,664,550 to Eick et al., entitled "Method and Apparatus for Detecting Left Ventricular Lead Displacement Based Upon EGM Change", appears to disclose a method for detecting the displacement of a left-ventricular electrode lead and the electrode poles thereof, by way of a changed signal amplitude, morphology or a changed time interval from an atrial signal.

Typically, the methods for detecting an electrode dislocation used with a left-ventricular electrode lead, such as a coronary sinus electrode lead, are limited since the electrode lead is implanted in a vein. As such, if dislocation occurs, it is often displaced within the vein by "only" a few millimeters to a few centimeters. In one or more embodiments, the parameters "signal amplitude", "impedance" and "stimulation threshold" may be influenced only slightly, thereby making it impossible to reliably detect such a dislocation.

The stated disadvantages of the methods that have been commonplace so far are basically solved by the methods of the IEGM signal comparison proposed in Eick '550. However, the methods of signal analysis presented in Eick '550 are not sensitive enough to reliably distinguish normal IEGM excursions, such as different heart rates and extra systoles, from an actual electrode dislocation. In addition, it appears as though the system of Eick et al. does not make it possible to determine the extent of the dislocation and to adapt the CRT stimulation accordingly.

BRIEF SUMMARY OF THE INVENTION

Proceeding therefrom, it is an object of at least one embodiment the invention is based on the desire to improve the sensitivity and specificity of displacement detection to the greatest extent possible.

To this end, according to at least one embodiment the invention a cardiac therapy device and/or a cardiac monitoring device that may be connected or connectable to at least one electrode lead that comprises at least one first sensing electrode pole and at least one second sensing electrode pole. In at least one embodiment of the invention, first and the second sensing electrode poles may move relative to one another during operation of the cardiac therapy device and/or the cardiac monitoring device. In one or more embodiments of the invention, the cardiac therapy device and/or the cardiac monitoring device includes a dislocation detection unit, that is connected or connectable, at least indirectly, to the first and the second sensing electrode poles, and which, in order to detect dislocation, and is designed to evaluate detection or sensing times at the first sensing electrode pole and at the second sensing electrode pole relative to one another. In at least one embodiment, the detection times may be ascribable to a particular cardiac event, such that the dislocation detection unit may generate a dislocation signal if the relative time relationship of detection times to be ascribed to one type of cardiac event changes beyond a predetermined extent, or threshold, or a specifically determined extent compared to a previously recorded reference value.

In one or more embodiments of the invention, the cardiac therapy device and/or the cardiac monitoring device may be used to reliably detect a dislocation of a left-ventricular coronary sinus electrode at an early stage, thereby making it possible, for example, to utilize the detection information to automatically adapt a CRT stimulation to conditions that may have changed due to a dislocation.

Thus, the cardiac therapy device and/or the cardiac monitoring device according to at least one embodiment of the invention makes it possible, for example, to reliably detect and quantify the dislocation of a multipolar coronary sinus electrode and to automatically adapt the CRT stimulation accordingly.

By way of one or more embodiments, the cardiac therapy device and/or the cardiac monitoring device is preferably an implantable stimulator for stimulating the heart, which is connected to at least one multi polar coronary sinus electrode lead, also referred to as a CS electrode lead, and at least one further, cardiac non-CS electrode lead, wherein the electrode poles of all electrode leads are connected to a particular sensing unit that records a point in time of the cardiac stimulation at a particular electrode pole.

In at least one embodiment of the invention, an apparatus is provided for automatically detecting the dislocation of a multi polar, left-ventricular, electrode and a method is provided for determining the extent of the dislocation, such that the points in time of the left-ventricular sensing are recorded and evaluated at a plurality of electrode poles with respect to a reference time, and the CRT stimulation is automatically adapted to the changed electrode position.

By way of one or more embodiments, the dislocation detection unit is preferably designed to determine a time difference between two detection times to be ascribed to a particular cardiac event as a relative value that describes the relative time relationship. Furthermore, in at least one embodiment, the dislocation detection unit compares the relative value to a reference value, wherein the reference value may be determined from one or more relative values of one or more prior cardiac cycles. If the relative value changes, such as the time difference between two detection times changes, for example, a detection time may have shifted with respect to time compared to the detection time determined at a second location for the same cardiac event. In at least one embodiment, such a time shift is an indication of spatial displacement of the first sensing electrode pole with respect to the second sensing electrode pole and, therefore, may also be an indication of a dislocation of the electrode lead.

In one or more embodiments of the invention, the cardiac therapy device and/or the cardiac monitoring device preferably comprises a stimulation unit, that is connected or connectable to a stimulation electrode pole, wherein the dislocation detection unit is designed to determine the relative time relationship of the detection times of a particular stimulated event, and to use the detected relative time relationship to detect a dislocation. In at least one embodiment, a stimulated event is generated for dislocation detection, which results in a defined cardiac constellation, such that the stimulation site is known and is reproducible, thereby improving the specificity of the dislocation detection.

According to one or more embodiments, the stimulation unit is preferably an atrial stimulation unit, and the stimulation electrode pole is preferably an atrial stimulation electrode pole for placement in the atrium of a heart.

By way of one or more embodiments of the invention, the first electrode lead including the first sensing electrode pole may be a coronary sinus electrode lead. The advantages of at least one embodiment of the invention become apparent in particular because previously known approaches for dislocation detection are not reliable enough in the case of a CS electrode lead.

The second sensing electrode pole is preferably part of a right-ventricular and/or a right-atrial electrode lead.

In at least one embodiment of the invention, the dislocation detection unit preferably comprises an evaluation unit that, within the scope of time analysis, evaluates time differences, of particular detection times or sensing times, of the excitation relative to a reference signal originating from the non-CS electrode lead in such a way that a dislocation is indicated given adequate temporal displacement of the sensing times, and the extent of the displacement is determined by evaluating at least two CS electrode poles.

In one or more embodiments of the invention, the cardiac therapy device and/or the cardiac monitoring device preferably comprises a stimulation control unit that is connected to at least one stimulation unit and is designed to control the delivery of a particular stimulation pulse via at least one determinable stimulation electrode pole depending on the dislocation signal.

In this context it is particularly preferable for the dislocation detection unit to deliver a dislocation signal that reflects an extent of a time shift of detection times or sensing times with respect to the previously detected reference value, that is, the extent of the change of the time difference between the detection time at the first sensing electrode pole and at the second sensing electrode pole. In a particularly preferred variant embodiment, the stimulation control unit may determine one of several stimulation electrode poles depending on the extent of the time shift.

According to one or more embodiments of the invention, if the first electrode lead including the at least one first sensing electrode pole is a CS electrode lead, the stimulation control unit is preferably designed to induce an automatic switch of the CS stimulation site depending on the extent of the dislocation, and/or may shut off the stimulation if the dislocation is extreme.

In at least one embodiment of the invention, the dislocation detection unit is preferably designed to perform a time analysis for detecting a dislocation, if a defined cardiac constellation is detected or set by the cardiac therapy device and/or the cardiac monitoring device, in order to thereby obtain adequate specificity and sensitivity. Such a defined cardiac constellation, for example, may be set by overstimulation of the atrium, in an AAI or A00 stimulation mode, approximately above the natural frequency.

Alternatively, such a defined cardiac constellation may be set via overstimulation of the right ventricle, in an RV-VVI or RV-V00 stimulation mode, approximately above the natural frequency. Overstimulation of the right ventricle may be appropriate for patients with an ablated AV node.

In at least one embodiment of the invention, the dislocation detection unit may recognize that a defined cardiac constellation is given when the cardiac therapy device and/or the cardiac monitoring device detects a phase to be classified as physical rest. For example, this may occur when an activity sensor, such as an accelerometer, delivers an output signal that indicates physical rest and/or if a timer delivers a time signal that indicates a typical resting time, such as nocturnal sleeping time.

According to one or more embodiments, the dislocation detection unit may perform dislocation detection retrospectively by utilizing detection times that were recorded in the past. They are preferably detection times that were recorded in a time period in which a particular (according to the day, for example) minimal heart rate occurred.

Alternatively or in addition thereto, in at least one embodiment, the dislocation detection unit may recognize that such a defined cardiac constellation is given when the cardiac therapy device and/or the cardiac monitoring device detects a phase of low heart rate variability. In at least one embodiment, the cardiac therapy device and/or the cardiac monitoring device may determine a Standard Deviation of the Averages of Normal Sinus to Normal Sinus (SDANN). The SDANN value, may be the standard deviation of the NN intervals, such as the R-R intervals, of the mean value in a limited time period; for example of 5 minutes.

Alternatively or in addition thereto, in one or more embodiments, the dislocation detection may perform dislocation detection only if the heart rate is located in a defined heart rate window, to also permit detection of patients with rate-dependent interventricular heart blocks. Such a defined heart rate window may therefore also be a defined cardiac constellation, within the scope of the invention.

A defined cardiac constellation to which the dislocation detection unit responds, in at least one embodiment, may include a combination of the previously described embodiments.

In at least one embodiment of the invention, when the first electrode lead including the at least one first sensing electrode pole is a CS electrode lead, the dislocation detection unit may perform a time analysis for dislocation detection that contains a time correction based on an interventricular signal transit time. The interventricular signal transit time may be measured using at least 2 CS electrode poles for this purpose, such that the specificity of the dislocation detection may be increased.

In one or more embodiments of the invention, a cardiac therapy device and/or a cardiac monitoring device, enables reliable dislocation detection even when a CS electrode lead is connected and used, and allows for quantification of the dislocation and, on the basis thereof, adaptation to the left-ventricular stimulation site.

According to at least one embodiment, the cardiac therapy device and/or the cardiac monitoring device may be an implantable biventricular cardiac pacemaker and/or a cardioverter/defibrillator. Such a device may be used, in particular, to perform cardiac resynchronization therapy (CRT).

BRIEF DESCRIPTION OF THE DRAWINGS

The invention will now be explained in greater detail with reference to exemplary embodiments and the figures. Shown are.

DETAILED DESCRIPTION OF THE INVENTION

Figure 1:
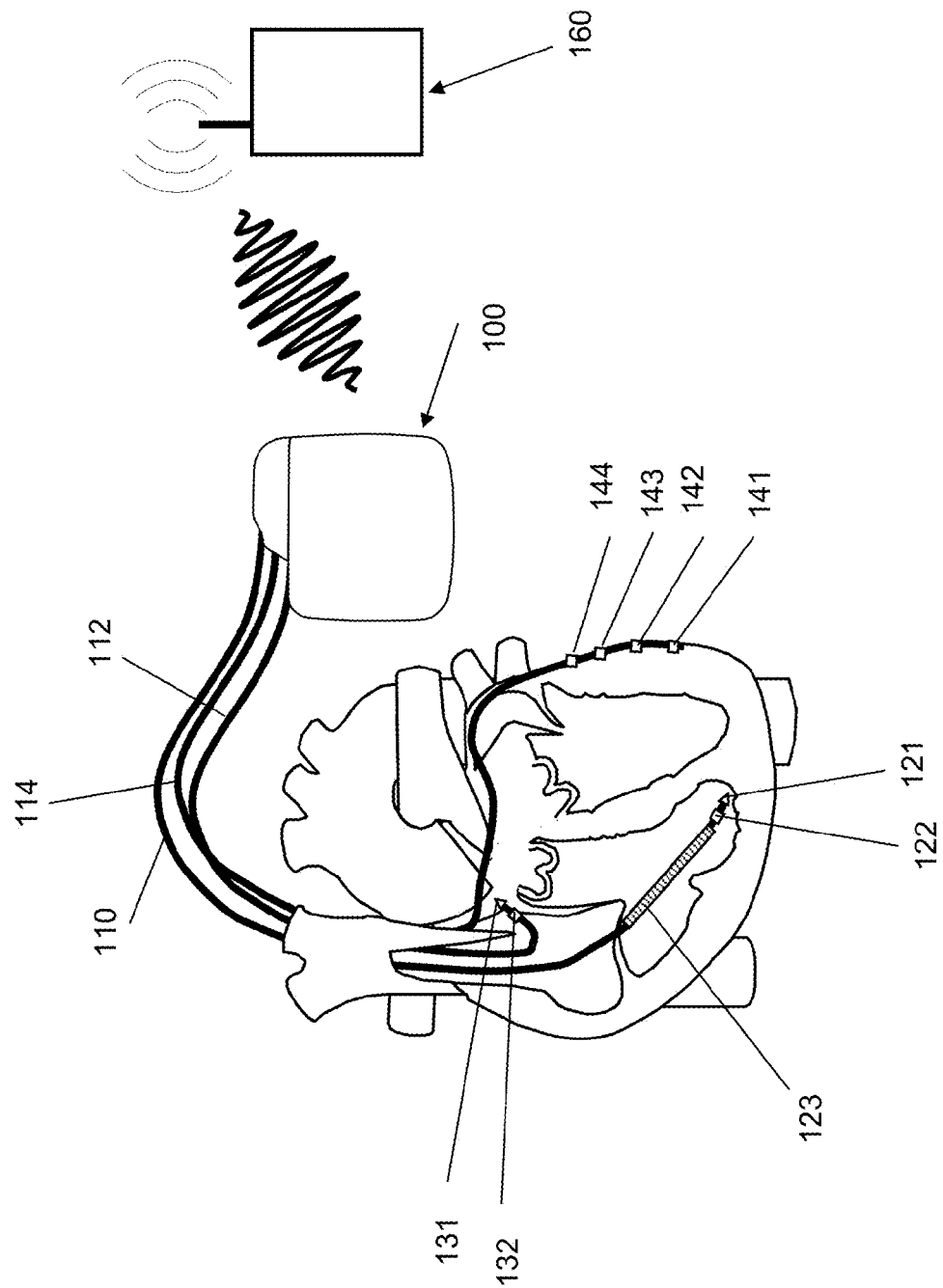
FIG. 1: A system comprising a cardiac therapy device and/or a cardiac monitoring device as an implantable CRT stimulator in the form of a three-chamber ICD system.

A three-chamber ICD system is shown in FIG. 1 as an example of a cardiac therapy device and/or a cardiac monitoring device. In one or more embodiments, the three-chamber ICD system includes an implantable device 100, such as the cardiac therapy device and/or the cardiac monitoring device that is connected to a plurality of implantable electrode leads 110, 112 and 114. In at least one embodiment of the invention, a right-ventricular (RV) electrode lead 110 is provided for right-ventricular sensing and stimulation, which includes a right-ventricular tip electrode (RV tip) 121 and a right-ventricular ring electrode (RV ring) 122 at a distal end. Right-ventricular stimulation pulses for biventricular CRT stimulation may be delivered via the RV tip electrode 121, as needed, during operation. In one or more embodiments, a distal shock coil (RV coil), or electrodes, 123 and, optionally, a proximal shock coil (not shown) may be installed on the electrode lead 110 to deliver a defibrillation shock. In this case, one or more counter electrode may form a housing of the implantable device 100, which is, at least in part, conductive.

According to one or more embodiments of the invention, a right-atrial electrode lead 112 includes, at a distal end thereof, a bipolar sensing and stimulation pole with a right-atrial tip electrode (RA tip) 131 and a right-atrial ring electrode (RA ring) 132, which may be used to sense an atrial rhythm and may be used for atrial stimulation, as necessary.

By way of one or more embodiments, the system may include a left-ventricular CS electrode lead for delivering left-ventricular stimulation pulses for CRT, using one or more, of a total of four, left-ventricular (CS) stimulation electrode poles 141, 142, 143 and 144. In one or more embodiments, the left-ventricular stimulation electrode pole 141 may be referred to as a left-ventricular tip electrode (LV tip), and the left-ventricular electrode poles 142, 143 and 144 may be referred to as left-ventricular ring electrodes (LV ring).

In at least one embodiment of the invention, a wireless, bidirectional telemetry unit may be provided in the implantable device 100 for communication with external programming and control, and data transmission devices 160.

Figure 2:
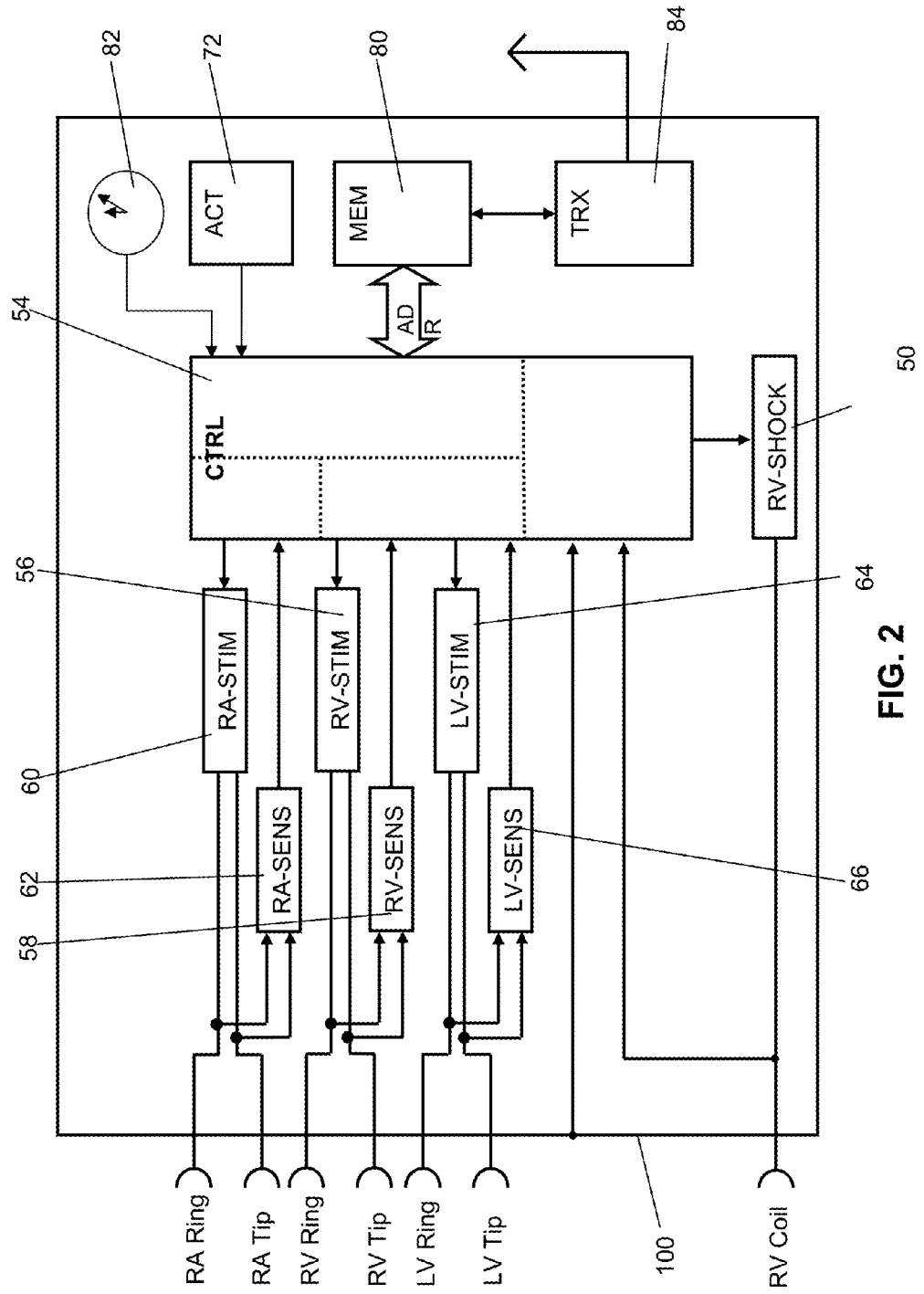
FIG. 2: the main components of the cardiac therapy device and/or the cardiac monitoring device of FIG. 1.

FIG. 2 illustrates the main components of the cardiac therapy device and/or the cardiac monitoring device of FIG. 1, according to at least one embodiment of the invention. FIG. 2 shows the main components of the implantable device 100, with electrical connections for the various electrodes 121 (RA Tip), 122 (RA Ring), 131 (RV Tip) and 132 (RV Ring) as shown on the left side. In one or more embodiments, the shock electrodes 123 are connected to a right-ventricular shock pulse generator 50 via an RV Coil connection. In at least one embodiment of the invention, the shock pulse generator 50 is connected to a stimulation control unit 54, which controls the shock pulse generator 50, as needed, to generate and deliver a defibrillation shock.

According to one or more embodiments, the connection for the right-ventricular tip electrode 131 (RV Tip) and the connection for the right-ventricular ring electrode 132 (RV Ring) are both connected to a right-ventricular stimulation unit 56 and a right-ventricular sensing unit 58, respectively. The right-ventricular stimulation unit 56 and the right-ventricular sensing unit 58 are both connected to the stimulation control unit 54.

In at least one embodiment of the invention, the right-ventricular stimulation unit 56 may generate a right-ventricular stimulation pulse in response to a trigger signal from the stimulation control unit 54, and deliver the right-ventricular stimulation pulse in the connection for the right-ventricular ring electrode RV Ring 132 and the right-ventricular tip electrode RV Tip 131. As an alternative, or in addition to, the housing of the implantable device 100 may form a neutral electrode, the right-ventricular stimulation unit 56 may be connected to the connection for the right-ventricular ring electrode RV Tip 131, and the housing may form another electrode for delivering a stimulation pulse. In one or more embodiments, a right-ventricular stimulation pulse differs from a defibrillation shock, in that the pulse intensity of the stimulation pulse is substantially lower, and so, unlike a defibrillation shock, it does not stimulate all of the cardiac tissue (myocardium) of a ventricle at once, but rather the cardiac muscle cells in the immediate vicinity of the right-ventricular tip electrode RV Tip 131. This stimulation then propagates by natural conduction across the entire right ventricle, thereby stimulating contraction of the right ventricle.

By way of one or more embodiments, the right-ventricular sensing unit 58 may initially amplify and filter electrical potentials present at the connection for the right-ventricular ring electrode RV Ring 132 and the right-ventricular tip electrode RV Tip 131 using an input amplifier. Furthermore, in at least one embodiment, the right-ventricular sensing unit 58 may evaluate a course of electrical signals present at inputs thereof in such a way that the right-ventricular sensing unit 58 automatically detects a natural (intrinsic), and automatic, contraction of the right ventricle. This may take place, for example, by comparing the course of the signal present at the inputs of the right-ventricular sensing unit 58 with a threshold value. Typically, the greatest amplitude of the signal in the form of an R peak is characteristic of a natural contraction of the right ventricle, which may be detected by comparison with a threshold value. In response thereto, the right-ventricular sensing unit 58 may output a corresponding output a signal indicating a natural contraction of the right ventricle to the stimulation control unit 54. As such, the point in time at which the threshold value is exceeded, is the detection time of the particular event.

In one or more embodiments of the invention, not shown in FIG. 2, one or more sensing units may be provided for the shock electrodes in the same manner. The one or more sensing units are preferably designed to detect signals between the shock electrodes, between the shock electrode 123 and the housing of the implantable housing 100, and/or between the other shock electrode and the housing of the implantable device 100.

In at least one embodiment, the connection of the right-atrial tip electrode 121 (RA Tip) and the connection of the right-atrial ring electrode 122 (RA Ring), may be connected to a right-atrial stimulation unit 60 and a right-atrial sensing unit 62, each of which is connected to the stimulation control unit 54. In one or more embodiments, the right-atrial stimulation unit 60 is designed to generate stimulation pulses having an intensity that is sufficient to stimulate the right-atrial myocardium, and the right-atrial stimulation pulses may have a pulse intensity that differs from that of the right-ventricular stimulation pulses. In at least one embodiment, the right-atrial sensing unit 62 may detect a P wave on the basis of the course of the differential signal present at the inputs thereof, wherein the P wave characterizes a natural (intrinsic) contraction of the right atrium. If the right-atrial sensing unit 62 detects a P wave, it may generate an output signal and may forward the output signal to the stimulation control unit 54, wherein the output signal characterizes a natural contraction of the right atrium.

By way of one or more embodiments, in the same manner, the connection of the left-ventricular tip electrode 141 LV Tip and the connections of the left-ventricular ring electrodes LV Ring 142, 143 and 144, wherein only the LV Ring connection is shown for simplicity, are also connected to a left-ventricular sensing unit 64 and a left-ventricular sensing unit 66. In one or more embodiments, the left-ventricular stimulation unit 64 and the left-ventricular sensing unit 66 may also be connected to the stimulation unit 54, wherein both the left-ventricular stimulation unit 64 and the left-ventricular sensing unit 66 may function in a manner similar to the above-described stimulation units 56 and 60 and sensing units 58 and 62.

Although not specifically shown in FIG. 2, the system may include a switching unit that makes it possible to connect any combination of the electrodes 141, 142, 143 and 144 to the inputs of the left-ventricular stimulation unit 64 and the left-ventricular sensing unit 66. In order to enable simultaneous detection of a plurality of left-ventricular signals, according to at least one embodiment, a separate sensing unit that (not shown in FIG. 2) may be provided for each of the left-ventricular electrodes 141, 142, 143, 144. In at least one embodiment, a separate stimulation unit (not shown in FIG. 2) may also be provided for the simultaneous delivery of a plurality of left-ventricular stimulation pulses via a plurality of the left-ventricular ring electrodes 141, 142, 143, 144.

By way of one or more embodiment of the invention, the implantable device 100 may include an acceleration sensor 72 connected to the stimulation control unit 54 and is integrated in the housing of the implantable device 100. In at least one embodiment, the acceleration sensor 72 is designed to detect a motion signal that is dependent on a patient's physical activity, and may output a corresponding first accelerometer output signal that indicates the patient's physical activity to the stimulation control unit 54. This makes it possible for the stimulation control unit 54 to adapt the timing of the stimulation pulses to the patient's needs, such as hemodynamic demand. The accelerometer output signal may also be used to determine resting phases in which dislocation detection may take place.

In at least one embodiment, the implantable device 100 may include a memory unit 80, connected to the stimulation control unit 54, wherein the implantable device 100 enables memory unit 80 to store signals that were generated or evaluated by the stimulation control unit 54. In at least one embodiment, the memory unit 80 may store control programs, in changeable and non-transitory form, for the stimulation control unit 54. Furthermore, the stimulation control unit 54 may be connected to a timer 82.

In one or embodiments of the invention, the memory unit 80 may be connected to a telemetry unit 84, which enables data stored in the memory unit 80 to be transmitted wirelessly to external device 160, or enables the external device 160 to transmit programming commands to the implantable device 100 and store the programming commands in the memory unit 80.

Figure 5:
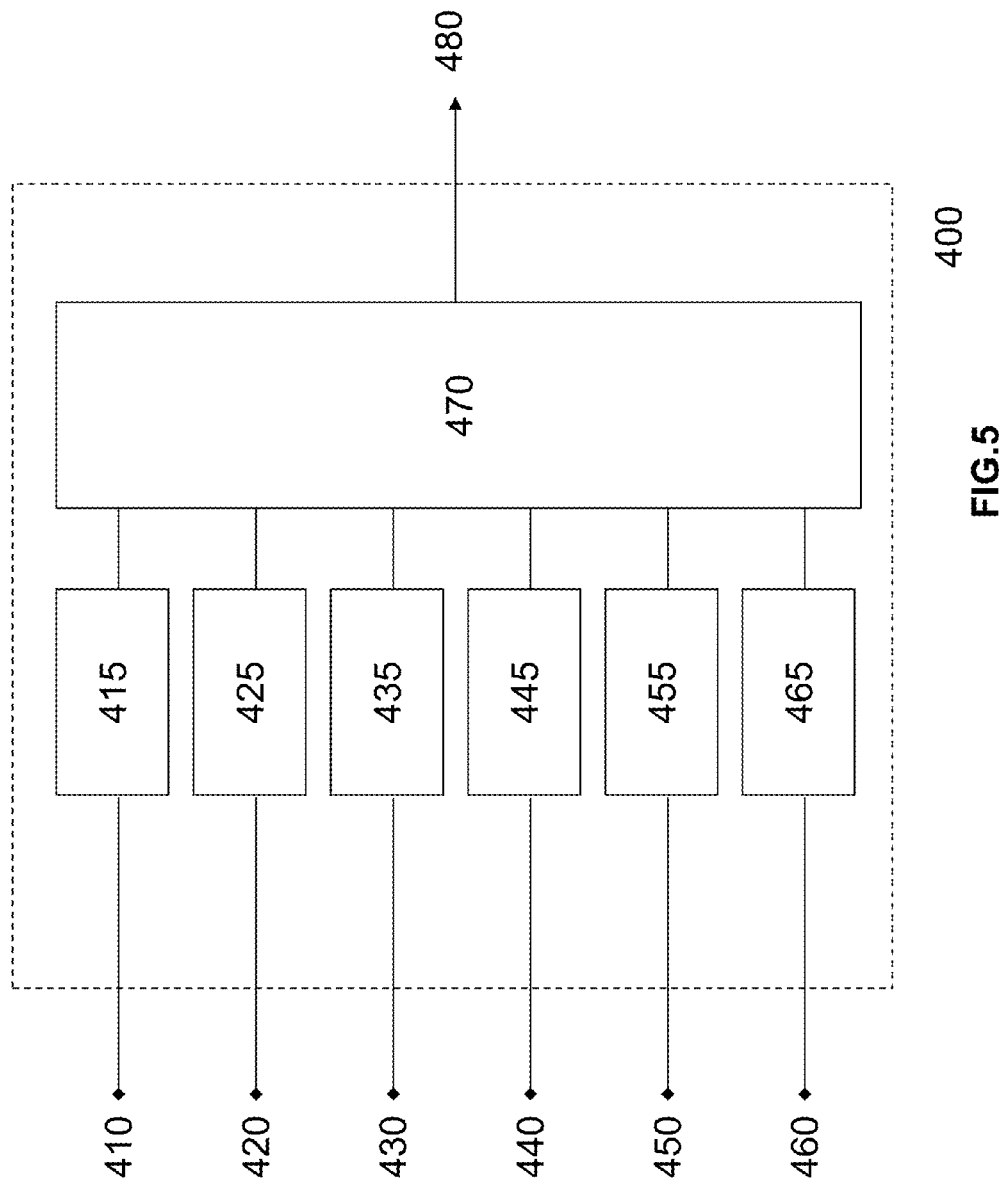
FIG. 5: a block diagram of a dislocation detection unit.
Figure 6:
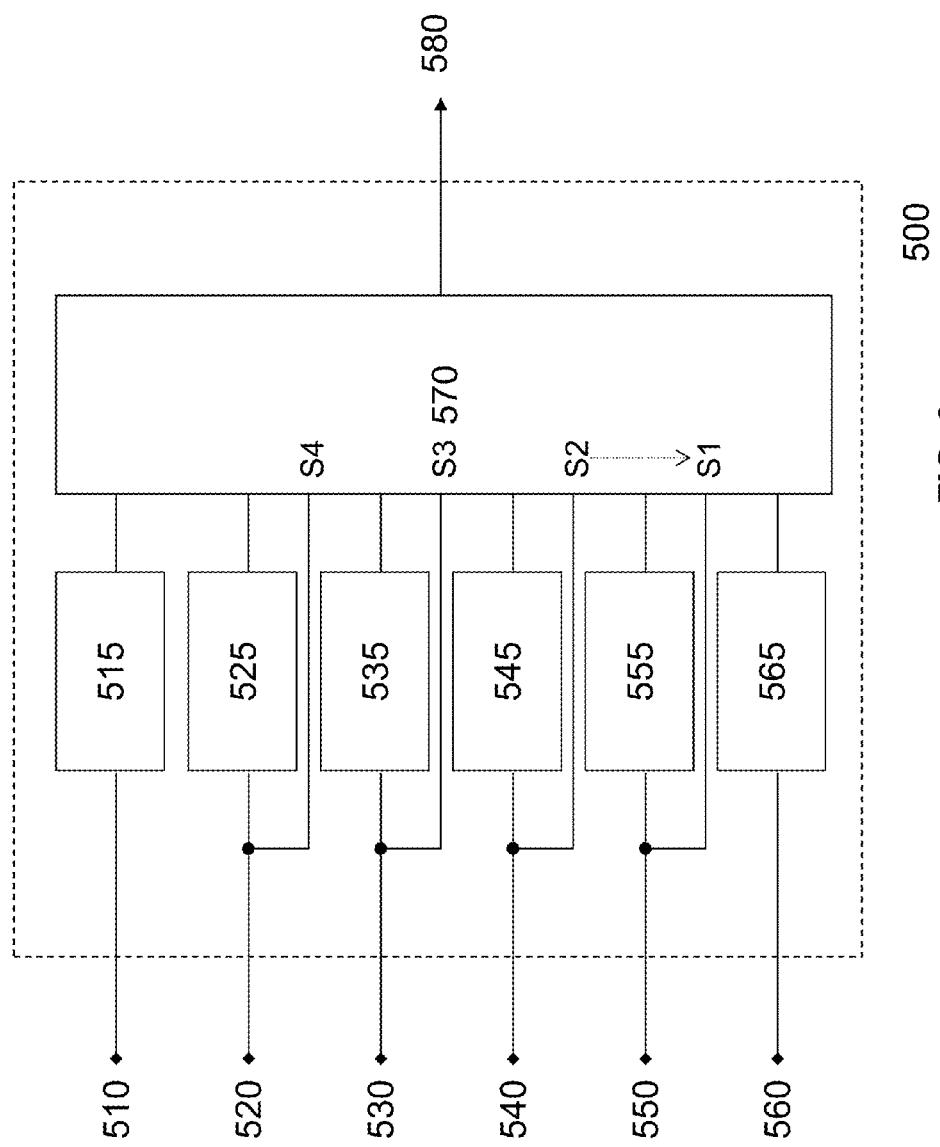
FIG. 6: a block diagram of an alternative variant embodiment.

According to one or more embodiments, the above described dislocation detection unit and the evaluation unit thereof, may be components of the stimulation control unit 54, as shown in FIG. 5 and FIG. 6.

Figure 3:
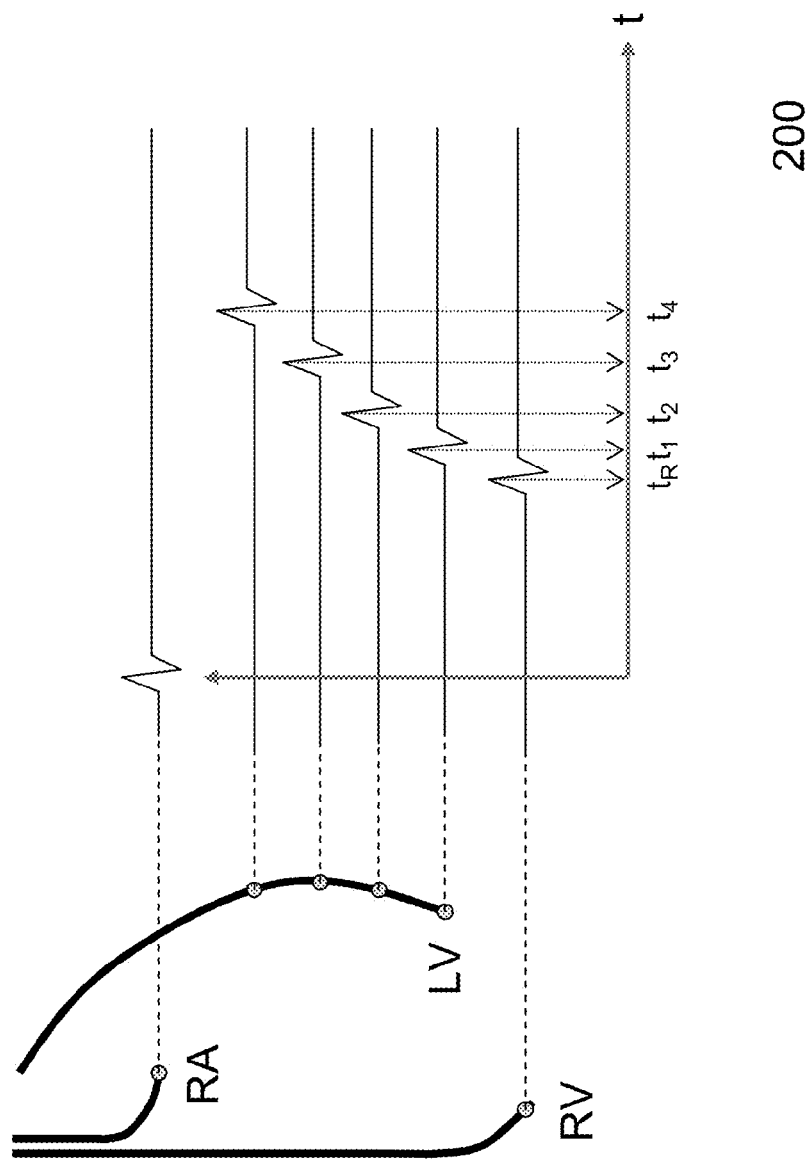
FIG. 3: the starting position of the electrode system and the time relationships of the one or more left-ventricular sensing compared to the signals that can be reference times.

FIG. 3 illustrates the starting position of the electrode system and the time relationships of the one or more left-ventricular sensing compared to the signals that can be reference times, according to at least one embodiment of the invention. As shown in FIG. 3, a starting position of the electrode system and the time relationships of the one or more left-ventricular sensing (t1 . . . t4) compared to the signals, may be reference times in the right atrium (RA=0) or the right ventricle (RV=tR). In one or more embodiments, the one or more left-ventricular sensing take place via the four left-ventricular (CS) stimulation electrode poles 141, 142, 143 and 144, each of which functions as a first sensing electrode pole. In one or more embodiments, the sensing electrode pole at the right-atrial electrode lead 112 or the sensing electrode pole at the right-ventricular electrode lead 110 each forms the second (reference) sensing electrode pole.

Figure 4:
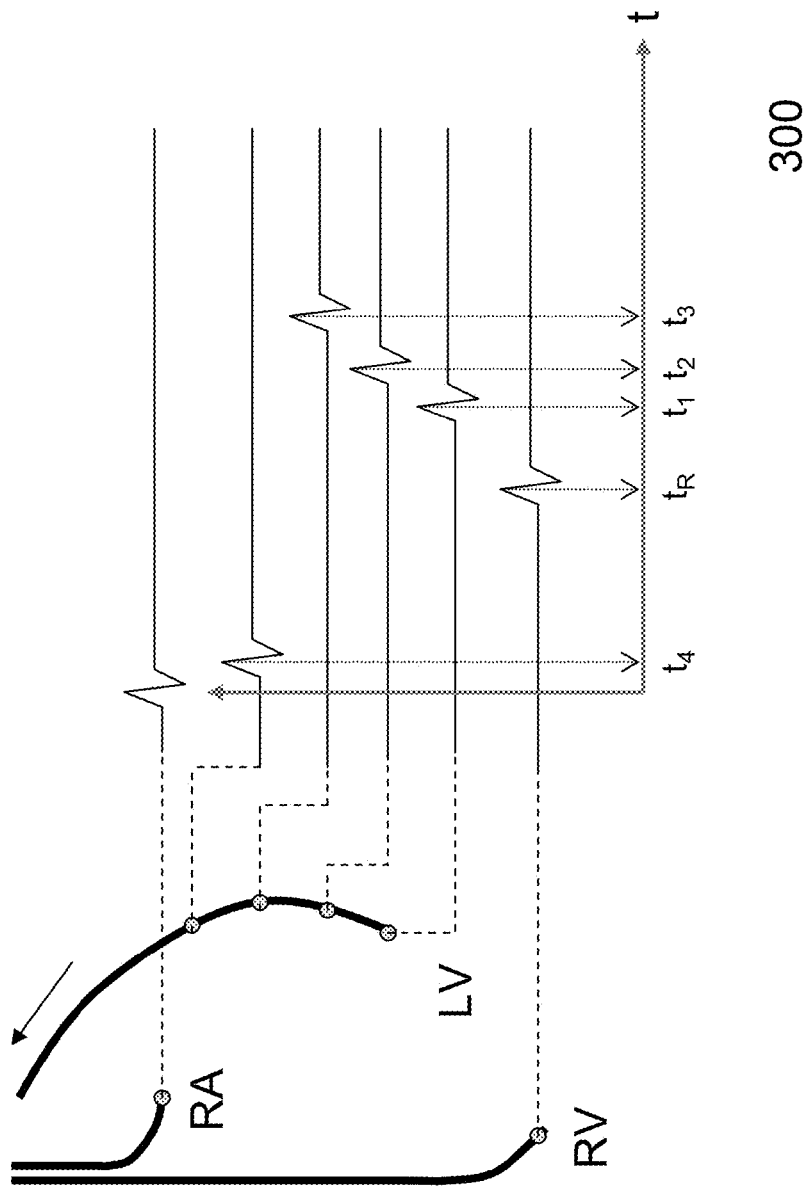
FIG. 4: a moderately dislocated CS electrode (LV

FIG. 4 illustrates a moderately dislocated CS electrode (LV), according to at least one embodiment of the invention, including a dislocated CS electrode lead (LV). As compared to FIG. 2, the CS electrode lead (LV) has moved proximally by a few millimeters, and therefore the actual CRT stimulation site is no longer achieved in an optimal manner. In at least one embodiment of the invention, the points in time of the left-ventricular sensing that are detected using common sensing units have shifted accordingly, as t1 to t3 are sensed with delay. Since the fourth electrode pole is now located in the region of the left atrium, a much earlier sense event (t4) is now sensed.

In one or more embodiments, on the basis of the above described time shift, it may be easily possible to determine, using an evaluation unit as a component of a dislocation detection unit, that the CS electrode was displaced proximally by approximately the distance of one ring. Optionally, in response thereto, in at least one embodiment, the stimulation control unit may correct the stimulation site for the CRT stimulation, for example, by switching from pole 2 to pole 1.

In one or more embodiments of the invention, to improve the specificity of the evaluation, the corresponding reference times are evaluated according to different courses of stimulation and therefore, for example, the heart rate and/or the intraventricular conduction times may be detected in a characteristic space of the analysis. It is therefore possible to compensate for regular IEGM excursions, such as circadian fluctuations of the conduction times for extra systoles, etc.

FIG. 5 illustrates a block diagram of a dislocation detection unit 400 according to at least one embodiment of the invention. In one or more embodiments of the invention, the right-atrial electrode 410, the four CS electrode poles 420, 430, 440, 450 and the right-ventricular electrode 460 are each connected to a sensing unit 415, 425, 435, 445, 455 and 465, respectively, to permit detection of a point in time of cardiac stimulation at the electrode pole. In at least one embodiment, these points in time are recorded in an evaluation unit 470 and are initially stored in a matrix for reference purposes. In one or more embodiment, the reference matrix is stored, for example, for various stimulation states of the heart, for different heart rates, etc. In at least one embodiment, instead of the dislocation detection unit 400 comprising separate units 415, 425, 435, 445, 455 and 465, it may access the sensing units 58, 62 and 66.

FIG. 6 illustrates an expanded block diagram of an alternative variant embodiment according to at least one embodiment of the invention. According to one or more embodiments, FIG. 6 corresponds to the block diagram of FIG. 5, with the addition of a switch of the CRT stimulation configuration, depending on the extent of dislocation that was determined as discussed previously. In the example shown in FIG. 4, for example, the electrode is displaced by approximately the distance of one ring, and therefore the stimulation site is now shifted from pole S2 to S1. As such, stimulation may still take place at a hemodynamically optimal site, despite the dislocation. In one or more embodiments, the switch may be implemented in the stimulation control unit 54 and may respond to an output signal from the dislocation detection unit 400, the evaluation unit 470 or the evaluation unit 570.

In at least one embodiment of the invention, if the dislocation is sufficient and extreme that the hemodynamically favorable stimulation site may no longer be reached, the stimulation configuration of the CRT system may be switched to a backup mode, depending on the programming, in order to prevent a stimulation that is not necessary and that may worsen the cardiac insufficiency.

Figure 7:
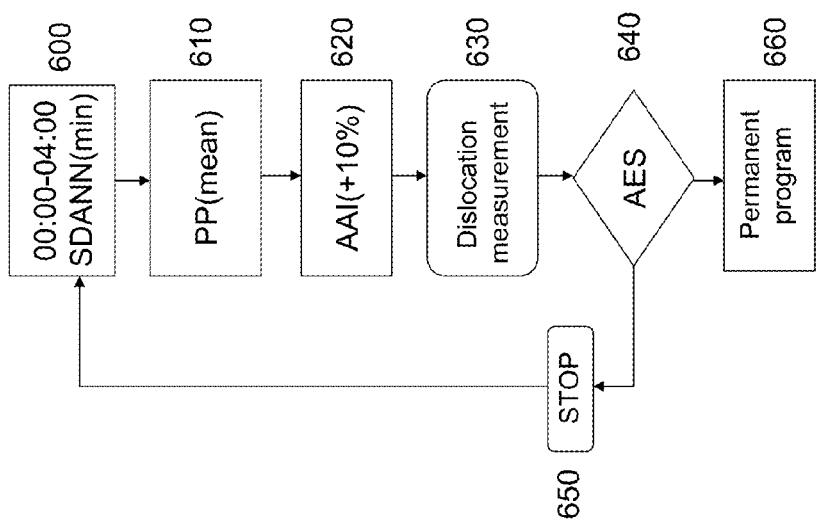
FIG. 7: a flow chart of an implementation of the dislocation analysis according to one or more embodiments the invention.

FIG. 7 illustrates a flow chart of an implementation of the dislocation analysis according to one or more embodiments the invention. In at least one embodiment, first, a check is carried out to determine whether the defined cardial constellation may be accepted 600. In this example, the analysis is started only at night and additionally only if the parameter SDANN is below a limit value determined from a trend mean value. Therefore, circadian, and other disturbance variables of the autonomous regulation of the stimulation conduction times that influence the measurement, are minimized. Next, according to one or more embodiments, the mean atrial frequency 610 may be determined and, based thereon, an AAI mode having a stimulation frequency above the atrial frequency is set 620. Since the propagation of electrical pulses has been defined, the actual dislocation analysis 630 may be carried out. In at least one embodiment, this analysis takes place, for example, for approximately 1-5 minutes in order to obtain very specific, detailed and efficient results. Next, according to at least one embodiment, the validity of the measurement is checked 640. The criterion therefore is, for example, the number of atrial extra systoles or inhibited atrial stimulations 640. In at least one embodiment, if the number of atrial extra systoles or inhibited atrial stimulations 640 is too high, above a threshold, the measurement is discarded 650 and restarted, if necessary. In at least one embodiment, if validity has been verified, the stimulator switches back to a permanent program 660.

According to one or more embodiments, the invention offers the advantage that a dislocation of a CS electrode may be detected at an early point in time and may be automatically quantified, thereby making it possible to automatically correct the CRT stimulation configuration.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A medical device comprising:
    a cardiac therapy device and/or a cardiac monitoring device configured to connect to at least one electrode lead,
        wherein the at least one electrode lead comprises at least one first sensing electrode pole and at least one second sensing electrode pole, each configured to move relative to one another during operation of the cardiac therapy device and/or the cardiac monitoring device,
    wherein the cardiac therapy device and/or the cardiac monitoring device comprises
        a dislocation detection unit configured to indirectly or directly connect to the at least one first sensing electrode pole and the at least one second sensing electrode pole,
            wherein the dislocation detection unit comprises an evaluation unit, and her in the dislocation detection unit is configured to
            evaluate one or more detection times at the at least one first sensing electrode pole and at the at least one second sensing electrode pole, relative to one another, wherein said one or more detection times are ascribable to a particular cardiac event,
            generate a dislocation signal if a relative time relationship of detection times that are ascribable to the particular cardiac event changes
                beyond a predetermined value,
                or
                beyond a specifically determined value compared to a previously recorded reference value,
            generate a plurality of time differences between particular detection times of the at least one first sensing electrode pole and the at least one second sensing electrode pole,
            generate the dislocation signal given an adequate time shift of the detection times, and,
            determine a particular extent of the time shift by evaluating at least two time differences of the plurality of time differences that result between the at least one first sensing electrode pole and the at least one second sensing electrode pole.

2. The medical device according to claim 1, wherein the dislocation detection unit is further configured to determine a time difference between two detection times ascribed to a particular cardiac event, as a relative value that describes the relative time relationship, and further configured to compare a relative value to a reference value, wherein the reference value is configured to be determined from one or more relative values of one or more prior cardiac cycles.

3. The medical device according to claim 1, wherein the cardiac therapy device and/or the cardiac monitoring device further comprises a stimulation unit and a stimulation electrode pole, wherein the stimulation unit is configured to connect to the stimulation electrode pole, and wherein the dislocation detection unit is further configured to determine the relative time relationship of the one or more detection times of a particular stimulated event, and further configured to use the relative time relationship to detect a dislocation.

4. The medical device according to claim 3, wherein the stimulation unit is an atrial stimulation unit, and the stimulation electrode pole is an atrial stimulation electrode pole configured to be placed in the atrium of a heart.

5. The medical device according to claim 1, wherein the electrode lead comprising the first sensing electrode pole is a coronary sinus electrode lead.

6. The medical device according to claim 1, wherein the at least one second sensing electrode pole is part of a right-ventricular or right-atrial electrode lead.

7. The medical device according to claim 1, wherein the cardiac therapy device and/or the cardiac monitoring device further comprises a stimulation control unit configured to connect to at least one stimulation unit and is further configured to control the delivery of a stimulation pulse via at least one stimulation electrode pole depending on the dislocation signal.

8. The medical device according to claim 1, wherein the dislocation detection unit is further configured to deliver the dislocation signal that reflects an extent of a time shift of detection times with respect to the previously recorded reference value.

9. The medical device according to claim 8, wherein the cardiac therapy device and/or the cardiac monitoring device further comprises a stimulation control unit, wherein the stimulation control unit is configured to determine one of a plurality of stimulation electrode poles depending on the extent of the time shift.

10. The medical device according to claim 9, wherein the stimulation control unit is further configured to induce an automatic switch between the plurality of stimulation electrode poles at the electrode lead, depending on the extent of the dislocation, and shut off the stimulation if the dislocation is extreme or both said induce and said shut off.

11. The medical device according to claim 5, wherein the cardiac therapy device and/or the cardiac monitoring device further comprises a stimulation control unit, and wherein the stimulation control unit is further configured to induce an automatic switch between a plurality of stimulation electrode poles at the coronary sinus electrode lead depending on an extent of the dislocation, and shut off the stimulation if the dislocation is extreme or both said induce and said shut off.

12. The medical device according to claim 1, wherein the dislocation detection unit is further configured to perform a time analysis to detect a dislocation during a defined cardial constellation that was detected or set by the cardiac therapy device and/or the cardiac monitoring device.

13. The medical device according to claim 1, wherein the dislocation detection unit is further configured to perform a time analysis to detect a dislocation that contains a time correction based on an interventricular signal transit time.

14. The medical device according to claim 12, wherein the cardiac therapy device and/or the cardiac monitoring device is further configured to measure the interventricular signal transit time at the at least one first sensing electrode pole and at the at least one second sensing electrode pole of the electrode lead.

15. The medical device according to claim 5, wherein the cardiac therapy device and/or the cardiac monitoring device is further configured to measure an interventricular signal transit time at the at least one first sensing electrode pole and at the at least one second sensing electrode pole of the coronary sinus electrode lead.

16. The medical device according to claim 1, wherein the cardiac therapy device and/or the cardiac monitoring device is an implantable biventricular cardiac pacemaker and/or cardioverter/defibrillator.

17. A medical device comprising:
a cardiac therapy device and/or a cardiac monitoring device configured to connect to at least one electrode lead,
  wherein the at least one electrode lead comprises at least one first sensing electrode pole and at least one second sensing electrode pole, each configured to move relative to one another during operation of the cardiac therapy device and/or the cardiac monitoring device,
wherein the cardiac therapy device and/or the cardiac monitoring device comprises
  a dislocation detection unit configured to indirectly or directly connect to the at least one first sensing electrode pole and the at least one second sensing electrode pole,
    wherein the dislocation detection unit comprises an evaluation unit, and wherein the dislocation detection unit is configured to
      evaluate one or more detection times at the at least one first sensing electrode pole and at the at least one second sensing electrode pole, relative to one another, wherein said one or more detection times are ascribable to a particular cardiac event,
      generate a dislocation signal if a relative time relationship of detection times that are ascribable to the particular cardiac event changes
        beyond a predetermined value,
        or
        beyond a specifically determined value compared to a previously recorded reference value, and,
      deliver the dislocation signal that reflects an extent of a time shift of detection times with respect to the previously recorded reference value; and,
    a stimulation control unit, wherein the stimulation control unit is configured to determine one of a plurality of stimulation electrode poles depending on the extent of the time shift.

18. A medical device comprising:
a cardiac therapy device and/or a cardiac monitoring device configured to connect to at least one electrode lead,
  wherein the at least one electrode lead comprises at least one first sensing electrode pole and at least one second sensing electrode pole, each configured to move relative to one another during operation of the cardiac therapy device and/or the cardiac monitoring device,
wherein the cardiac therapy device and/or the cardiac monitoring device comprises
  a dislocation detection unit configured to indirectly or directly connect to the at least one first sensing electrode pole and the at least one second sensing electrode pole,
    wherein the dislocation detection unit comprises an evaluation unit, and wherein the dislocation detection unit is configured to
      evaluate one or more detection times at the at least one first sensing electrode pole and at the at least one second sensing electrode pole, relative to one another, wherein said one or more detection times are ascribable to a particular cardiac event,
      generate a dislocation signal if a relative time relationship of detection times that are ascribable to the particular cardiac event changes
        beyond a predetermined value,
        or
        beyond a specifically determined value compared to a previously recorded reference value, and,
      perform a time analysis to detect a dislocation during a defined cardial constellation that was detected or set by the cardiac therapy device and/or the cardiac monitoring device; and,
    wherein the cardiac therapy device and/or the cardiac monitoring device is further configured to measure the interventricular signal transit time at the at least one first sensing electrode pole and at the at least one second sensing electrode pole of the electrode lead.

19. A medical device comprising:
a cardiac therapy device and/or a cardiac monitoring device configured to connect to at least one electrode lead,
  wherein the at least one electrode lead comprises at least one first sensing electrode pole and at least one second sensing electrode pole, each configured to move relative to one another during operation of the cardiac therapy device and/or the cardiac monitoring device,
wherein the cardiac therapy device and/or the cardiac monitoring device comprises
  a dislocation detection unit configured to indirectly or directly connect to the at least one first sensing electrode pole and the at least one second sensing electrode pole,
    wherein the dislocation detection unit comprises an evaluation unit, and wherein the dislocation detection unit is configured to
      evaluate one or more detection times at the at least one first sensing electrode pole and at the at least one second sensing electrode pole, relative to one another, wherein said one or more detection times are ascribable to a particular cardiac event, and, generate a dislocation signal if a relative time relationship of detection times that are ascribable to the particular cardiac event changes beyond a predetermined value, or beyond a specifically determined value compared to a previously recorded reference value;

wherein the electrode lead comprising the first sensing electrode pole is a coronary sinus electrode lead; and, wherein the cardiac therapy device and/or the cardiac monitoring device is further configured to measure an interventricular signal transit time at the at least one first sensing electrode pole and at the at least one second sensing electrode pole of the coronary sinus electrode lead.

* * * * *